United States Patent [19]

Sugier et al.

[11] 4,257,920

[45] Mar. 24, 1981

[54] CATALYST CONTAINING A NOBLE METAL OF THE VIIITH GROUP, COPPER OXIDE, ZINC OXIDE AND A RARE EARTH METAL, ITS MANUFACTURE AND USE IN THE CONVERSION OF CARBON MONOXIDE

[75] Inventors: Andre Sugier, Rueil Malmaison; Philippe Courty, Houilles; Edouard Freund, Rueil Malmaison, all of France

[73] Assignee: Societe Francaise des Produits pour Catalyse, Rueil-Malmaison, France

[21] Appl. No.: 95,007

[22] Filed: Nov. 16, 1979

[30] Foreign Application Priority Data

Nov. 17, 1978 [FR] France ............................... 78 32704

[51] Int. Cl.$^3$ ..................... B01J 21/04; B01J 23/10; B01J 23/60; B01J 23/72

[52] U.S. Cl. .................. 252/462; 260/449.5; 423/656

[58] Field of Search ...................... 252/462; 260/449.5

[56] References Cited

U.S. PATENT DOCUMENTS

| 3,758,417 | 9/1973 | Magoon et al. ...................... 252/462 |
| 4,126,581 | 11/1978 | Sugier et al. ......................... 252/463 |

*Primary Examiner*—W. J. Shine
*Attorney, Agent, or Firm*—Millen & White

[57] ABSTRACT

Catalyst for producing hydrogen by reaction of carbon monoxide with water or for producing methanol by reaction of carbon monoxide with hydrogen, containing by weight 10–60% of copper oxide, 5–40% of zinc oxide, 1–20% of a rare earth metal oxide, 30–70% of aluminous cement and optionally 0.01–1% of a noble metal from group VIII.

6 Claims, No Drawings

CATALYST CONTAINING A NOBLE METAL OF THE VIIITH GROUP, COPPER OXIDE, ZINC OXIDE AND A RARE EARTH METAL, ITS MANUFACTURE AND USE IN THE CONVERSION OF CARBON MONOXIDE

Prior French Pat. No. 2,352,588 discloses a catalyst which contains by weight 10 to 60% of copper oxide, 5 to 40% of zinc oxide and 30 to 70% of an aluminous cement and its use in the conversion of carbon monoxide to produce hydrogen or menthanol. In addition French Pat. No. 2,113,467, describes a catalyst for producing methanol from carbon moxoxide, which catalyst contains copper and zinc oxides in a ratio by weight of copper to zinc in the range from 1:0.05 to 1:10 and from 1 to 25% by weight of didymium oxide (calculated as metal with respect to the catalyst).

It has now been found that the catalysts containing simultaneously from 10 to 60% (preferably 18 to 27%) by weight of copper oxide (calculated as CuO), from 5 to 40% by weight of zinc oxide (preferably from 15 to 26%) (calculated as ZnO), from 1 to 20% (preferably 3 to 15% and more particularly 4 to 7%) by weight of rare earth metal oxide (calculated as $M_2O_3$ where M is the rare earth metal) and from 30 to 70% by weight of aluminous cement (prerably 40 to 60%), show an increased activity and stability in the production of hydrogen by reacting carbon monoxide with steam and for synthesizing methanol from carbon monoxide and hydrogen. By rare earth metal is meant a metal having an atomic number from 57 to 71.

The rare earth metal oxides, used pure or as mixtures, are mainly lanthanum, cerium, neodymium and praseodymium oxides. Didymium oxide, a mixture of neodymium and praseodymium oxides, may also be used.

The preferred rare earth metal oxides are lanthanum, neodymium and praseodymium oxides.

According to a preferred embodiment, the catalyst may further contain 0.01 to 1% by weight of a noble metal from group VIII, particularly palladium, platinum and/or rhodium. Such a catalyst offers the advantage of avoiding to a large extent, in the methanol synthesis reaction, the formation of by-products and particularly of dimethylether.

The constituting elements, copper oxide, zinc oxide and rare earth metal oxide or their precursors, are admixed with an aluminous cement; water is added to obtain the hardening of the mixture. The shaping of the catalyst may be performed either before or after water addition, according to the used technique, for example by pelletizing or bowl granulation. Usually the operation is completed with a roasting step, for example at 200°-600° C.

The copper oxide, the zinc oxide and the rare earth metal oxide may be used as such, for example as CuO, ZnO, $Nd_2O_3$, $La_2O_3$, $CeO_2$, $Pr_2O_3$, or in the form of other compounds, for example salts. According to a preferred technique precursors are used, which consist of thermally decomposable salts such as nitrates, formates, acetates or carbonates. This decomposition is obtained by heating to a temperature of, for example, 200° to 600° C., for example during the above mentioned roasting step.

The shaping may be performed in any known manner, for example by pelletizing or preferably by bowl granulation. One of the advantages of making use of an aluminous cement is to enable the bowl granulation of the product even with a high content of active oxides (up to 70% by weight) while ensuring a very high mechanical strength and a very satisfactory stabilization of the active phase, which means that the catalyst is kept active over long periods.

By aluminous cement is meant a cement which contains, by weight, from 10 to 50% of CaO and/or BaO and from 30 to 85% of $Al_2O_3$, the total content of $CaO + BaO + Al_2O_3$ being at least 70% by weight. Other oxides may be present as impurities, for example $SiO_2$, $Fe_2O_3$ and $TiO_2$. The content of each of these oxides is preferably smaller than 10% by weight.

The main constituents of these cements are $Al_2O_3$, CaO (or $Al_2O_3$, BaO) and 2 $Al_2O_3$, CaO. In the final catalyst, the content of these aluminates is usually from 15 to 40%, preferably from 20 to 30% (analysis by X rays diffraction).

The use of aluminous cement is an essential characteristic of the invention. As a matter of fact, it has been observed that the use of a conventional cement, such as Portland cement, led to catalysts which rapidly lose their initial strength, particularly in the presence of steam.

The operation is completed by a roasting step, for example at 200°-600° C., preferably 325°-450° C.; reduction with hydrogen may be further performed, for example at 100°-400° C. By roasting is meant a heating in the presence of an oxygen-containing gas, for example air.

The setting of the cement may be favored by adding ammonium carbonate, for example as an aqueous solution; the preferred solutions will contain from 10 to 100 g of ammonium carbonate per liter.

The setting time of the cement is not an original characteristic per se. Setting times of one hour or more are usually satisfactory.

The conversion rates of CO and $CO_2$ with hydrogen conform essentially to the following schemes:

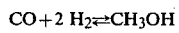

$$CO + 2 H_2 \rightleftharpoons CH_3OH$$

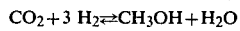

$$CO_2 + 3 H_2 \rightleftharpoons CH_3OH + H_2O$$

The operating conditions, in the presence of catalysts, are well known. Preferably, the pressure will be from 20 to 200 bars and the temperature from 200° to 300° C.

The conversion rate of carbon monoxide with steam is as follows:

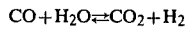

$$CO + H_2O \rightleftharpoons CO_2 + H_2$$

The operating conditions are also well known. Preferably the temperature will be from 150° to 350° C. and more preferably from 170° to 250° C.

By way of example, several catalysts have been prepared. Catalysts A and B' are reference catalysts, not in conformity with the invention.

Catalyst A is prepared as follows:

In a crusher, there is admixed 347 g of zinc carbonate containing 72% by weight of zinc oxide and 350 g of copper carbonate containing 72% by weight of copper oxide with 500 g of Super Secar Laffarge cement. The Super Secar Laffarge cement has the following average composition (in % by weight): $Al_2O_3 = 81$, $CaO = 17$, $Na_2O = 0.8$, $SiO_2 = 0.1$, $Fe_2O_3 = 0.1$, and a content of less than 0.1% for each of the other constituents. The resulting powder, whose grain size is smaller than 2 microns, is then bowl granulated to balls of a diameter from 4 to 7 mm in a rotary bowl granulator by spraying 275 ml of a 40 g/l aqueous solution of ammonium carbonate.

The balls are then matured for 12 hours at 40° C. in a steam saturated atmosphere and then maintained for 2 hours at 400° C. in air.

The resulting catalyst has a total pore volume of 32 ml/100 g, a surface of 153 m$^2$/g and its mechanical strength, measured in a LHOMARGI apparatus, is 24 kg. F. The analysis by X-ray diffraction indicates that the catalyst content of calcium aluminates $Al_2O_3$, CaO and 2 $Al_2O_3$, CaO is 26.4% by weight.

Composition by weight: CuO: 25.1%—ZnO: 24.9%—Cement: 50%

This catalyst does not contain a rare earth metal.

CATALYST B

In a crusher, there is admixed 312 g of zinc carbonate containing 72% by weight of zinc oxide, 315 g of copper carbonate containing 72% by weight of copper oxide and 93 g of lanthanum carbonate containing 54.1% of lanthanum oxide $La_2O_3$, with 500 g of Super Secar Laffarge cement. The resulting powder, whose grain size is smaller than 2 microns, is then bowl granulated to balls of a diameter from 4 to 7 mm in a rotating bowl granulator by spraying 275 ml of a 40 g/l aqueous solution of ammonium carbonate.

The balls are then matured for 12 hours at 40° C. in a steam saturated atmosphere, then maintained for 2 hours at 400° C. in air. The resulting catalyst has a pore volume of 32.5 ml/100 g and its mechanical strength, measured in the LHOMARGI apparatus, is 25 kgF; its specific surface is 158 m$^2$/g. The composition by weight is: CuO 22.6%, ZnO 22.4%, $La_2O_3$ 5%, cement: complement to 100%, i.e. 50%.

The X-ray diffraction analysis indicates that the calcium aluminates content of the catalyst is 24.5% by weight.

CATALYST B'

The preparation of catalyst B is repeated but without using cement. The resulting catalyst contains by weight: CuO: 45.2%, ZnO: 44.8%, $La_2O_3$: 10%.

CATALYST C

The operation is the same as for catalyst B, but the 93 g of lanthanum carbonate are replaced with 84.6 g of cerium carbonate containing 59.6% of cerium oxide $CeO_2$.

After thermal treatment, the composition by weight is: CuO 22.6%, ZnO 22.4%, $Ce_2O_3$ 5%, cement: complement to 100%, i.e. 50%.

The resulting catalyst has a pore volume of 32 ml/100 g and its mechanical strength is 24 kgF; its specific surface is 141 m$^2$/g.

The analysis by X diffraction indicates that the calcium aluminates content by weight of the catalyst is 24%.

CATALYST D

The operation is the same as for catalyst B but lanthanum carbonate is replaced by 75 g of didymium carbonate containing 67% by weight of neodymium and praseodymium oxides in a proportion of 30% by weight of praseodymium oxide and 70% by weight of neodymium oxide.

The resulting catalyst has a pore volume of 31.5 ml/100 g, its mechanical strength is 24.5 kgF and its specific surface is 155 m$^2$/g. It contains by weight: 22.6% of CuO, 22.4% of ZnO, 5% of didymium and 50% of cement.

The analysis by X diffraction indicates that the calcium aluminates content of the catalyst is 23.6% by weight.

CATALYST E

The procedure is the same as for catalyst D, except that the sprayed solution further contains 0.5 g of palladium as palladium chloride dissolved in 10 ml of water containing 2 ml of 10 N ammonia. The catalyst thus contains 0.06% by weight of palladium.

CATALYST F

The procedure is the same as for catalyst D, except that the sprayed solution further contains 0.5 g of rhodium as hexaamine chloride [Rh $(NH_3)_6]Cl_3$ dissolved in 10 ml of water containing 1 ml of 10 N ammonia. The catalyst thus contains 0.06% by weight of rhodium.

CATALYST G

The procedure is the same as for catalyst D, except that the sprayed solution further contains 0.5 g of platinum as tetramine platinum chloride. The catalyst contains 0.06% of platinum.

The specific surface, the pore volume, the mechanical strength and the calcium aluminate content of catalysts E, F and G are identical to those of catalyst D.

The catalyst activity in the conversion of carbon monoxide by water and by hydrogen is then measured for the different catalysts so prepared. This measure is performed after activation of the catalysts under atmospheric pressure, at 180° C., by passage of a gas containing by volume 1% of CO and 99% of nitrogen, for 48 hours with a VVH (gas volume/catalyst volume/hour) of 500.

EXAMPLE 1

The activity, for the conversion of carbon monoxide by water to $CO_2$ and $H_2$, of the so-prepared catalysts is measured as follows:

Over 100 ml of catalyst placed in a cylindrical reactor of a 30 mm diameter whose temperature is maintained at 195° C., there is passed a gas whose composition (in volume %) is:

CO=4

$CO_2$=23

$H_2$=70

$CH_4+N_2$=3 and steam (ratio of steam to gas at the inlet=0.8) at a VVH (volume of dry gas per volume of catalyst per hour) of 8500, under a pressure of 20 bars. At the outlet of the reactor, the gases are analyzed to determine the percentage of carbon monoxide converted to $CO_2$ and $H_2$.

$$\frac{\text{moles CO at the inlet} - \text{moles CO at the outlet}}{\text{moles CO at the inlet}}$$

The results are reported in the following table:

| CATALYYST | HOURS OF RUN | % CO CONVERTED |
|---|---|---|
| A | 1 | 96 |
|   | 100 | 93 |
| B | 1 | 98 |
|   | 100 | 95 |
| C | 1 | 97 |
|   | 100 | 94 |
| D | 1 | 97.5 |
|   | 100 | 96 |
| G | 1 | 97 |
|   | 100 | 95.6 |
| B' | 1 | 94.5 |
|   | 100 | 91 |

After 100 hours of test, the mechanical strength of the catalyst is measured in a LHOMARGI apparatus. The following results have been obtained.

TABLE II

| CATALYST | MECHANICAL STRENGTH kg F |
|---|---|
| A | 24 |
| B | 25 |
| C | 24 |
| D | 24.5 |
| B' | 24 |

EXAMPLE 2

The activity for the conversion of carbon monoxide by hydrogen to methanol is measured by passing over 100 ml of catalyst, under a pressure of 100 bars, at 250° C. and with a VVH (NTP gas volume per volume of catalyst per hour) of 8500, a gas of the following composition (in % by volume):

$CO = 4.5$ $CO_2 = 4$ $H_2 = 84$ $N_2 = 7.5$

At the reactor outlet, the products are analyzed and there is deduced therefrom the conversion by mole of methanol per mole of CO (Table III) and $CO_2$ (Table IV) at the reactor inlet.

The main results are reported in the following Tables III and IV giving the initial activity, i.e. after 48 hours of operation (t=48) and the activity after 200 hours of run (t=200).

TABLE III

| CATALYST | CONVERSION of CO to CH$_3$OH in % | | CONVERSION of CO to dimethylether in % | |
|---|---|---|---|---|
|   | t = 48 | t = 200 | t = 48 | t = 200 |
| A | 53.6 | 52.1 | 0.05 | 0.03 |
| B | 57.3 | 56 | 0.9 | 0.8 |
| C | 53.9 | 52.5 | 1.1 | 1.0 |
| D | 58.1 | 56.9 | 0.9 | 0.7 |
| E | 57.8 | 56.5 | 0.04 | 0.03 |
| F | 57.7 | 56.3 | 0.05 | 0.04 |
| G | 57.8 | 56.3 | 0.04 | 0.04 |
| B' | 52.8 | 51.6 | 1.2 | 1.2 |

TABLE IV

| CATALYST | CONVERSION of CO to CH$_3$OH in % | | CONVERSION of CO to dimethylether in % | |
|---|---|---|---|---|
|   | t = 48 | t = 200 | t = 48 | t = 200 |
| A | 43.3 | 41.9 | 0.04 | 0.02 |
| B | 47.2 | 46.0 | 0.7 | 0.6 |
| C | 43.5 | 42.2 | 1.0 | 0.9 |
| D | 47.5 | 46.4 | 0.7 | 0.6 |
| E | 47.3 | 46.1 | 0.03 | 0.02 |
| F | 47.1 | 46.1 | 0.03 | 0.03 |
| G | 47.0 | 46.0 | 0.03 | 0.03 |
| B' | 42.5 | 41.4 | 1.1 | 1.1 |

EXAMPLE 3

Another advantage of using a hydraulic cement for the preparation of the catalyst lies in the fact that the resultant catalysts are more resistant to poisoning by sulfur and are regenerable.

As a matter of face, when the charge contains sulfur compounds, it is observed that the catalysts containing a hydraulic cement are not only more resistant, but may be regenerated by roasting either in the presence of air, or in the presence of steam, or of a mixture of at least one of these two compounds with an inert gas used as diluent, for example nitrogen.

The regenerability of the catalysts is shown by the following tests.

Example 1 is repeated except that 500 parts per million by volume of $H_2S$ are added to the gas feed charge and the treatment is discontinued when the sulfur content of the catalyst is 5% by weight; then the activity of the catalyst for the conversion of carbon monoxide is determined as above described. Then, a controlled oxidation of the catalyst is performed by scavenging at 200° C. with 0.5% of oxygen in nitrogen. After the end of this step, the catalyst is heated for 4 hours at 400° C. in air, and then reduced at 200° C. with 1% of hydrogen in nitrogen and, finally, it is subjected to the activity test.

The following results were obtained:

TABLE V

| CATALYST | BEFORE REGENERATION | AFTER REGENERATION |
|---|---|---|
| A | 31 | 90 |
| B | 33 | 91 |
| C | 32 | 91 |
| D | 35 | 91 |
| G | 32 | 94.3 |

This example shows that catalyst G is regenerated more easily owing to platinum which seems to facilitate the reduction of the formed copper sulfate.

What is claimed is:

1. A catalyst containing from 0.01 to 1% by weight of a noble metal of the VIII$^{th}$ group, 10 to 60% by weight of a copper oxide, 5 to 40% by weight of zinc oxide, 1 to 20% by weight of at least one rare earth metal oxide, and 30 to 70% of aluminous cement, said aluminous cement comprising from 10 to 50% by weight of at least one oxide selected from CaO and BaO and 30 to 85% by weight of Al$_2$O$_3$, the total content of CaO, BaO and Al$_2$O$_3$ in said aluminous cement being at least 70% by weight.

2. A catalyst according to claim 1, containing from 3 to 15% by weight of rare earth metal oxide.

3. A catalyst according to claim 1, wherein said catalyst is produced such that an aluminous cement is admixed with a compound of a noble metal of the VIII$^{th}$ group, a copper compound, a zinc compound and a rare earth metal compound, the proportions, calculated as CuO, ZnO, rare earth metal oxide and aluminous cement being respectively 10 to 60%, 5 to 40%, 1 to 20% and 30 to 70% by weight in a dry state, and in that water is added and the mixture is shaped and heated to activate the catalyst.

4. A catalyst according to claim 3, wherein the mixture is shaped, before hardening of the cement.

5. A catalyst according to claim 4, wherein the catalyst is shaped by bowl granulation.

6. A catalyst according to claim 3, wherein ammonium carbonate is added to the mixture of the components.

* * * * *